United States Patent
Naoi et al.

(10) Patent No.: US 11,413,234 B2
(45) Date of Patent: Aug. 16, 2022

(54) TRANSPARENT COMPOSITION AND TRANSPARENT COSMETIC

(71) Applicant: SHISEIDO COMPANY, LTD., Tokyo (JP)

(72) Inventors: Kayoko Naoi, Kanagawa (JP); Kouichi Nagai, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 32 days.

(21) Appl. No.: 16/606,802

(22) PCT Filed: Apr. 12, 2018

(86) PCT No.: PCT/JP2018/015402
§ 371 (c)(1),
(2) Date: Oct. 21, 2019

(87) PCT Pub. No.: WO2018/198800
PCT Pub. Date: Nov. 1, 2018

(65) Prior Publication Data
US 2020/0375874 A1 Dec. 3, 2020

(30) Foreign Application Priority Data
Apr. 26, 2017 (JP) .............................. JP2017-087082

(51) Int. Cl.
| | | |
|---|---|---|
| *A61K 8/81* | (2006.01) | |
| *A61K 8/02* | (2006.01) | |
| *A61K 8/25* | (2006.01) | |
| *A61K 8/37* | (2006.01) | |
| *A61K 8/44* | (2006.01) | |
| *A61K 8/73* | (2006.01) | |
| *A61K 8/88* | (2006.01) | |
| *A61Q 17/04* | (2006.01) | |

(52) U.S. Cl.
CPC .......... *A61K 8/8147* (2013.01); *A61K 8/0229* (2013.01); *A61K 8/25* (2013.01); *A61K 8/37* (2013.01); *A61K 8/44* (2013.01); *A61K 8/731* (2013.01); *A61K 8/8111* (2013.01); *A61K 8/88* (2013.01); *A61Q 17/04* (2013.01); *A61K 2800/48* (2013.01); *A61K 2800/594* (2013.01); *A61K 2800/624* (2013.01)

(58) Field of Classification Search
None
See application file for complete search history.

(56) References Cited

U.S. PATENT DOCUMENTS

| | | |
|---|---|---|
| 5,223,250 A | 6/1993 | Mitchell et al. |
| 2004/0185019 A1 | 9/2004 | Beachy et al. |
| 2005/0079188 A1 | 4/2005 | Ohmori et al. |
| 2009/0280076 A1 | 11/2009 | Yoshida et al. |
| 2017/0290760 A1 | 10/2017 | Nakano et al. |
| 2017/0333301 A1 | 11/2017 | Yamaki et al. |
| 2019/0046421 A1 | 2/2019 | Yamaki et al. |

FOREIGN PATENT DOCUMENTS

| | | |
|---|---|---|
| JP | H01-163111 A | 6/1989 |
| JP | H02-180805 A | 7/1990 |
| JP | H02-264707 A | 10/1990 |
| JP | H04-91010 A2 | 3/1992 |
| JP | H09-235210 A2 | 9/1997 |
| JP | 2003-113023 A | 4/2003 |
| JP | 2005-213145 A | 8/2005 |
| JP | 2007-314459 A | 12/2007 |
| WO | 2014/203913 A1 | 12/2014 |
| WO | 2016/039369 A1 | 3/2016 |
| WO | 2016/068298 A1 | 5/2016 |
| WO | 2016/068300 A1 | 5/2016 |
| WO | 2017/061604 A1 | 4/2017 |

OTHER PUBLICATIONS

Anonymous, "Day Care Revolution W II SPF 30 PA+++", Mintel, Mar. 3, 2017, Database GNPD [online], XP055762461, total 5 pages; Cited in EESR.
Extended European Search Report (EESR) dated Feb. 5, 2021 issued in the corresponding European Patent Application No. 18792135.8.
Japanese Office Action dated Feb. 17, 2021 issued in the corresponding Japanese Patent Application No. 2017-087082 and its English translation.
International Search Report (ISR) dated Jul. 17, 2018 filed in PCT/JP2018/015402.
International Search Opinion dated Jul. 17, 2018 filed in PCT/JP2018/015402 and its partial English translation.
Japanese Office Action dated Oct. 6, 2021 for corresponding Japanese Patent Application No. 2017-087082 and its English translation.
Chinese Office Action dated May 10, 2022 issued in Chinese patent application No. 201880026759.3 and its English translation, 15 pages.

*Primary Examiner* — Melissa L Fisher
(74) *Attorney, Agent, or Firm* — Rankin, Hill & Clark LLP

(57) ABSTRACT

A transparent composition having UV protection effect is provided, wherein the UV protection effect is improved after the composition is contacted with moisture, such as water or sweat, more than that immediately after the composition is applied, while maintaining high transparency. The transparent composition contains (a) a UV absorbent, (b) an oil component having a refractive index in the range from 1.5 to 1.7, (c) an oil component having a refractive index of not less than 1.3 and less than 1.5, and (d) a powder having a refractive index in the range from 1.45 to 1.55, wherein a mixed oil component obtained by mixing the (b) oil component having a refractive index in the range from 1.5 to 1.7 and the (C) oil component having a refractive index of not less than 1.3 and less than 1.5 has a refractive index in the range from 1.44 to 1.56.

8 Claims, No Drawings

TRANSPARENT COMPOSITION AND TRANSPARENT COSMETIC

CROSS-REFERENCE TO RELATED APPLICATIONS

This application is a National Phase Entry of PCT International Application No. PCT/JP2018/015402 filed on Apr. 12, 2018, which claims priority under 35 U.S.C § 119(a) to Japanese Patent Application 2017-087082 filed on Apr. 26, 2017. Each of the above applications is hereby expressly incorporated by reference, in its entirety, into the present application.

TECHNICAL FIELD

The present disclosure relates to a transparent composition having high UV protection effect, and a transparent cosmetic containing the transparent composition as a base.

BACKGROUND ART

Various transparent bases for oil-based transparent cosmetics are studied for their advantages mainly regarding beauty of appearance and clear finish when the cosmetic is applied.

For example, Japanese Unexamined Patent Publication No. H1-163111 (hereinafter, Patent Literature 1) discloses a cosmetic using a transparent base that comprises 12-hydroxystearic acid and an oil component and has a refractive index in the range from 1.45 to 1.54. Further, Japanese Unexamined Patent Publication No. H2-264707 (hereinafter, Patent Literature 2) discloses a transparent solid cosmetic that comprises 12-hydroxystearic acid, heavy liquid paraffin, and an oil-based liquid component, and Japanese Unexamined Patent Publication No. H4-91010 (hereinafter, Patent Literature 3) discloses a transparent solid cosmetic that comprises 12-hydroxystearic acid, a transparent oil-based liquid component having a hydroxyl value of not more than 120, and methyl phenyl polysiloxane.

Still further, Japanese Unexamined Patent Publication No. H9-235210 (hereinafter, Patent Literature 4) discloses, as a transparent cosmetic containing a dextrin fatty acid ester, a transparent solid cosmetic that contains a dextrin fatty acid ester, heavy liquid paraffin, and an oil-based liquid component, in view of improving gloss when the cosmetic is applied. Yet further, Japanese Unexamined Patent Publication No. 2005-213145 (hereinafter, Patent Literature 5). discloses a transparent solid composition that contains a dextrin fatty acid ester, a volatile oil component, an oil component having a refractive index in the range from 1.4 to 1.6, and a spherical powder having a refractive index in the range from 1.3 to 1.6 and an average particle diameter in the range from 3 to 30 µm, in view of exerting an unevenness compensation effect on the skin to make the pores of skin unnoticeable.

While transparent cosmetics containing the above-mentioned 12-hydroxystearic acid or a dextrin fatty acid ester are widely known, such transparent solid cosmetics have a problem that, when another active ingredient is added to make the cosmetic exert an additional effect, formability, stability, or transparency of the cosmetic is impaired.

Japanese Unexamined Patent Publication No. 2007-314459 (hereinafter, Patent Literature 6) discloses a transparent solid cosmetic that is thickened or gelled with an amino acid derivative-modified silicone, wherein a transparent solid composition contains a specific lysine derivative-modified silicone, a silicone oil, a polar oil component having an IOB (Inorganic Organic Balance) value in the range from 0.17 to 0.63, and a UV absorbent, in view of maintaining transparency of the appearance even when a UV absorbent that has poor solubility in a non-polar oil component is added.

While the transparent cosmetic disclosed in Patent Literature 6 contains a UV absorbent, a cosmetic applied to the skin, in general, is exposed to various types of moisture from inside and outside the layer of the cosmetic, such as sweat secreted onto the skin, and moisture from external environment, such as sea water. Even when a high amount of resin or coating agent to impart water resistance is added the cosmetic, it is difficult to completely prevent a UV absorbent or a UV scattering agent from being washed out, and therefore lowering of the UV protection effect is inevitable.

On the other hand, the present applicant has proposed an emulsion sunscreen cosmetic (WO 2016/068298 and WO 2016/068300, hereinafter, Patent Literature 7 and 8) that uses an oil component thickener, etc., and has a non-conventional characteristic that the UV protection effect is improved after the composition is contacted with moisture, such as water or sweat, more than that immediately after the composition is applied.

SUMMARY

As disclosed in Patent Literature 6, while transparent cosmetics containing a UV absorbent are known, there is a problem that, when such a cosmetic contacts moisture, such as water or sweat, the UV absorbent, etc., are washed out and the resulting UV protection effect becomes lower than that immediately after the cosmetic is applied. In order to minimize lowering of the UV protection effect due to contact with moisture, such as water or sweat, it is considered to apply an oil component thickener, as taught in Patent Literature 7 and 8. However, in the case of a transparent cosmetic, there is a problem that, when another active ingredient is added to make the cosmetic exert an additional effect, stability as well as transparency, which is the primary function of the cosmetic, are impaired.

In view of the above-described circumstances, the present disclosure is directed to providing a transparent composition having UV protection effect and a characteristic that the UV protection effect is improved after the composition is contacted with moisture, such as water or sweat, more than that immediately after the composition is applied, while maintaining high transparency.

Solution to Problem

The present inventor has found through intensive study to solve the above-described problem that a transparent composition that exhibits higher UV protection effect than that immediately after the composition is applied, while maintaining high transparency, can be produced by adding, to a UV absorbent and an oil component thickener, two types of oil components each having a refractive index within a certain range and a powder having a refractive index within a certain range, and accomplished the disclosure.

Namely, a transparent composition the present disclosure comprises:
(a) a UV absorbent;
(b) an oil component having a refractive index in the range from 1.5 to 1.7;
(c) an oil component having a refractive index of not less than 1.3 and less than 1.5; and (d) a powder having a refractive index in the range from 1.45 to 1.55, wherein a mixed oil component obtained by mixing the (b) oil component having a refractive index in the range from 1.5 to 1.7 and the (C) oil component having a refractive index of not less than 1.3 and less than 1.5 has a refractive index in the range from 1.44 to 1.56.

It is preferred that the transparent composition of the disclosure further comprise (e) an oil component thickener.

It is preferred that the (d) powder having a refractive index in the range from 1.45 to 1.55 be polymethyl methacrylate, silica, nylon, cellulose, polyethylene, polyurethane, or a copolymer or a coated product comprising any of them.

It is preferred that a mass ratio of the (d) powder having a refractive index in the range from 1.45 to 1.55 relative to the (a) UV absorbent be not less than 0.01 and mot more than 1.

It is preferred that the (e) oil component thickener be a dextrin fatty acid ester, a sucrose fatty acid ester, a glyceryl fatty acid ester, an amino acid-based gelling agent, a fatty acid or a salt thereof, or an organic modified clay mineral.

It is preferred that the transparent composition of the disclosure be provided in a solid form, and the solid form may be a stick form.

A transparent cosmetic of the disclosure comprises the above-described transparent composition as a base.

The transparent composition of the present disclosure has a characteristic that, even when the composition contacts moisture, such as water or sweat, the UV protection effect is improved more than that immediately after the composition is applied while maintaining high transparency, and thus can provide high UV protection effect.

DESCRIPTION OF EMBODIMENTS

Now, a transparent composition of the present disclosure will be described in detail.

The transparent composition of the disclosure (which may hereinafter be simply referred to as "composition") comprises:

(a) a UV absorbent;
(b) an oil component having a refractive index in the range from 1.5 to 1.7;
(c) an oil component having a refractive index of not less than 1.3 and less than 1.5; and
(d) a powder having a refractive index in the range from 1.45 to 1.55, wherein a mixed oil component obtained by mixing the (b) oil component having a refractive index in the range from 1.5 to 1.7 and the (C) oil component having a refractive index of not less than 1.3 and less than 1.5 has a refractive index in the range from 1.44 to 1.56.

The individual components are described below.

(a) UV Absorbent

The (a) UV absorbent (which may hereinafter be simply referred to as "(a) component") used in the disclosure is not particularly limited and selected from those able to be added to agents that are externally applied to the skin, such as cosmetics; however, it is preferred that the UV absorbent be an oil-soluble absorbent. Specific examples thereof may include t-butyl methoxydibenzoylmethane, ethylhexyl methoxycinnamate (octylmethoxycinnamate), phenyl salicylate, octyl salicylate, homomenthyl salicylate (homosalate), ethylhexyl salicylate, octocrylene, 2-hydroxy 4-methoxybenzophenone, polysilicon-15, ethylhexyl triazone, ethylhexyl triazone, hexyl diethylamino hydroxybenzoyl benzoate, bis-ethylhexyl oxyphenol methoxyphenyl triazine, oxybenzone-3, methylene bis-benzotriazolyl tetramethylbutylphenol, 2,4,6-trianilino-p-(carbo-2'-ethylhexyl-1'-oxy)-1,3,5-triazine, hexyl 2-[4-(diethylamino)-2-hydroxybenzoyl]benzoate, 2,4-bis-[{4-(2-ethylhexyloxy)-2-hydroxy}-phenyl]-6-(4-methoxyphenyl)-1,3,5-triazine, dolometrizole trisiloxane, etc.

In particular, t-butyl methoxydibenzoylmethane, ethylhexyl methoxycinnamate, homomenthyl salicylate, octyl salicylate, octocrylene, and 2-hydroxy 4-methoxybenzophenone, etc., can preferably be used in the composition of the disclosure.

The UV absorbent may be used alone or in combination of two or more, as appropriate.

The UV absorbent is contained in an amount in the range from 3 to 50 mass %, and preferably in the range from 5 to 35 mass %, relative to the total amount of the composition.

It is preferred that the transparent composition of the disclosure be free of a scattering agent, and if a scattering agent is contained, it is desirable that the content of the scattering agent be not more than 0.1 mass %. Adding a scattering agent to the transparent composition may render the composition cloudy and reduce the transparency of the composition, and therefore is not preferred.

(b) Oil Component having a Refractive Index in the Range from 1.5 to 1.7

The (b) oil component having a refractive index in the range from 1.5 to 1.7 (which may hereinafter be simply referred to as "(b) component" or "high refractive index oil component") is an oil component that have a relatively high refractive index in the range from 1.5 to 1.7 at 25° C. Examples of such a high refractive index oil component may include, but are not limited to, hydrogenated polyisobutene, trimethylpentaphenyl polysiloxane, diphenylsiloxy phenyl trimethicone, diphenyl dimethicone, phytosteryl macadamia nut fatty acid, phytosteryl isostearate, etc. Examples of commercially available product of trimethyl pentaphenyl polysiloxane include PH-1555HRIC (having a refractive index of 1.58) available from Dow Corning Toray, silicone KF56 (having a refractive index of about 1.5) available from Shin-Etsu Chemical Co., Ltd., and FZ-3156 (having a refractive index of 1.575) available from Nippon Unicar. An example of commercially available product of diphenyl dimethicone is KF-54 (having a refractive index of 1.505) available from Shin-Etsu Chemical Co., Ltd. An example of commercially available product of phytosteryl macadamia nut fatty acid is Plandool-MAS (having a refractive index of 1.501) available from Nippon Fine Chemical. These products may be used suitably.

The high refractive index oil component having a refractive index in the range from 1.5 to 1.7 is contained in the transparent composition of the disclosure in such an amount that a mixed oil component obtained by mixing the high refractive index oil component and the (c) oil component having a refractive index of not less than 1.3 and less than 1.5, which will be described later, has an average refractive index in the range from 1.44 to 1.56. The content of the high refractive index oil component may vary depending on the types and combination of other components, and preferably in the range from 5 to 50 mass %, more preferably in the range from 10 to 40 mass %, and even more preferably in the range from 15 to 35 mass % relative to the composition.

The high refractive index oil component may be used alone or in combination of two or more, as appropriate.

(c) Oil Component having a Refractive Index of Not Less than 1.3 and Less than 1.5

The (c) oil component having a refractive index of not less than 1.3 and less than 1.5 (which may hereinafter be simply referred to as "(c) component" or "low refractive index oil component") is an oil component that has a relatively low refractive index of not less than 1.3 and less than 1.5 at 25° C. Examples of such a low refractive index oil component may include, but are not limited to, diisopropyl sebacate (having a refractive index of about 1.43), triethylhexanoine (having a refractive index of about 1.45), isopropyl myristate (having a refractive index of about 1.43), hydrogenated polydecene (having a refractive index of about 1.46), glyceryl tricaprylate-caprate (having a refractive index of about 1.45), glyceryl tri-2-ethylhexanoate (having a refractive index of about 1.44), cetyl 2-ethylhexanoate (having a refractive index of about 1.44), trimethylolpropane trioctanoate (having a refractive index of about 1.45), squalane (having a refractive index of about 1.45), α-olefin oligomer (having a refractive index of about 1.46), glyceryl diisostearate (having a refractive index of about 1.46), and diisostearyl malate (having a refractive index of about 1.46), polyglyceryl triisostearate (having a refractive index of about 1.47), macadamia nut oil (having a refractive index of about 1.47), liquid paraffin (having a refractive index of about 1.47), isododecane (having a refractive index of about 1.42), isohexadecane (having a refractive index of about 1.43), light isoparaffin (having a refractive index of about 1.43), dimethylpolysiloxane (having a refractive index of about 1.40), polyoxyalkylene-polyalkylsiloxane (alkylene=ethylene: having a refractive index of about 1.42), and the like. In particular, diisopropyl sebacate, triethylhexanoine, and glyceryl tricaprylate-caprate, etc, can preferably be used.

In view of usability, the (c) component may contain a volatile oil component having a boiling point of not higher than 300° C. at normal pressure. Adding the volatile oil component to the (c) component allows mitigating greasiness, thereby providing less sticky finish.

The low refractive index oil component is contained in the transparent composition of the disclosure in such an amount that a mixed oil component obtained by mixing the low refractive index oil component and the above-described high refractive index oil component has an average refractive index in the range from 1.44 to 1.56. The content of the low refractive index oil component may vary depending on the types and combination of other components, and preferably in the range from 5 to 50 mass %, more preferably in the range from 10 to 40 mass %, and even more preferably in the range from 15 to 35 mass % relative to the composition.

The low refractive index oil component may be used alone or in combination of two or more, as appropriate.

The content of the mixed oil component obtained by mixing the high refractive index oil component (the (b) component) and the low refractive index oil component (the (c) component) is not particularly limited; however, preferably in the range from 10 to 80 mass %, and more preferably in the range from 20 to 70 mass %. If the content of the oil components is less than 10 mass %, it may be difficult to impart glossy finish to the composition. On the other hand, if the content of the oil components exceeds 80 mass %, the composition may become sticky. The contents of the (b) component and the (c) component are adjusted such that the mixed oil component thereof has an average refractive index in the range from 1.44 to 1.56.

(d) Powder having a Refractive Index in the Range from 1.45 to 1.55

The (d) powder having a refractive index in the range from 1.45 to 1.55 (which may hereinafter be simply referred to as "(d) component") is a powder having a refractive index in the range from 1.45 to 1.55 (literature value). By using a powder having a refractive index in this range, a difference between the refractive index of the powder and the refractive index of the oil-based components used in the disclosure is small, and this allows accomplishing a highly transparent base. Examples of such a powder may include, but are not limited to, silica, dimethyl silylated silica (about 1.46), polymethyl methacrylate (about 1.49), HDI/trimethylol hexyl lactone cross polymer (about 1.5), IPDI/poly (1,4-butane diol)-14 cross polymer (about 1.49), nylon (about 1.53), cellulose (about 1.49), polyethylene (about 1.51), polyurethane (about 1.50), anhydrous silicic acid (about 1.45 to 1.50), etc. Further, such a powder may be subjected to a surface treatment, such as hydrophobization, according to a conventional method before the powder is added.

Examples of commercially available product of hydrophobic silica may include AEROSIL R972, R972V, R972CF, R974, R976, and R976S (available from NIPPON AEROSIL Co., Ltd.), which are products treated with dimethyl dichlorosilane, AEROSILR805 (available from NIPPON AEROSIL Co., Ltd.), which is a product treated with octyl silane, AEROSIL R812, R812S, and RX200 (available from NIPPON AEROSIL Co., Ltd.), which are products treated with hexamethyldisilazane, and AEROSIL R202 and RY200 (available from NIPPON AEROSIL Co., Ltd.), which are products treated with dimethyl silicone oil.

Further, the polymethyl methacrylate may be a spherical powder mainly composed of a cross-linked polymethacrylic acid (PMMA) and may contain other components, such as silica, in an amount of not more than several mass %.

Examples of commercially available product of the polymethyl methacrylate may include GANZPEARL GMX-0810 (available from Ganz Chemical Co., Ltd.) and MICROSPHERE M-330 (available from Matsumoto Yushi Seiyaku Co., Ltd.).

Examples of commercially available product of the anhydrous silicic acid may include SUNSPHERE L-51, L-31, H-31, H-31, NP-30, and NP-100 (available from AGC Si-Tech Co., Ltd.).

The polyurethane may be a spherical powder mainly composed of an urethane resin and may contain other components, such as silica, in an amount of not more than several mass %.

An example of commercially available product of the polyurethane is TP POWDER U series (available from Toshiki Pigment Co., Ltd.).

The powder is contained in an amount in the range from 0.1 to 20 mass %, and preferably in the range from 0.5 to 10 mass % relative to the total amount of the composition. Matching the refractive indices of the oil component and the powder allows providing a transparent composition even when a substantial amount of the powder is added, and allows reducing stickiness and increase usability while maintaining high transparency. Further, in a case where a volatile oil component is contained with such a powder, the composition has a transparent appearance before the composition is applied, and then becomes semi-transparent when the composition is applied to the skin since the volatile oil component is volatilized and the refractive indices of the powder and the oil component are shifted from each other, and this allows providing unevenness compensation effect.

A mass ratio of the (d) component relative to the (a) UV absorbent is preferably not less than 0.01 and not more than 1, and more preferably not less than 0.01 and not more than 0.5. Providing the mass ratio of the (d) component relative to the (a) component within this range allows enhancing the effect that the UV protection effect is improved when the composition contacts with moisture.

(e) Oil Component Thickener

It is preferred that the transparent composition of the disclosure contain an (e) oil component thickener.

The (e) oil component thickener (which may hereinafter be simply referred to as "(e) component") can be selected as appropriate from materials that are used in cosmetics, etc., as a component exerting an effect of thickening an oil component by being dissolved in or swelled with the oil component. Preferred examples of the (e) oil component thickener may include a dextrin fatty acid ester, a sucrose fatty acid ester, a glyceryl fatty acid ester, an amino acid-based gelling agent, a fatty acid or a salt thereof, or an organic modified clay mineral. The oil component thickener may be used alone or in combination of two or more, as appropriate, and it is particularly preferred that the oil component thickener be used in combination of two or more.

The dextrin fatty acid ester is an ester of a dextrin or a reduced dextrin and a higher fatty acid, and a dextrin fatty acid ester usable in the disclosure is not particularly limited as long as it is commonly used in cosmetics. It is preferred to use a dextrin or a reduced dextrin having an average sugar polymerization degree in the range from 3 to 100. Further, as a constituent fatty acid of the dextrin fatty acid ester, it is preferred to use a saturated fatty acid having a carbon number in the range from 8 to 22. Specific examples thereof may include dextrin palmitate, dextrin oleate, dextrin stearate, dextrin myristate, and dextrin palmitate/2-ethylhexanoate.

As the sucrose fatty acid ester, a sucrose fatty acid ester having a fatty acid that is linear or branched, saturated or unsaturated, and has a carbon number in the range from 12 to 22 can preferably be used. Specific examples thereof may include sucrose caprylate, sucrose caprate, sucrose laurate, sucrose myristate, sucrose palmitate, sucrose stearate, sucrose oleate, and sucrose erucate.

The glyceryl fatty acid ester is an esterified reaction product that is obtained by reacting glycerin, a dibasic acid having a carbon number in the range from 18 to 28, and a fatty acid (other than dibasic acids) having a carbon number in the range from 8 to 28, and a glyceryl fatty acid ester usable in the disclosure is not particularly limited as long as it is commonly used in cosmetics. Specific examples thereof may include glyceryl behenate/isostearate/eicosanedioate, glyceryl behenate/eicosanedioate, and polyglyceryl-10 behenate/eicosanedioate.

Specific examples of the amino acid-based gelling agent may include dibutyl lauroyl glutamide, dibutyl ethylhexanoyl glutamide, polyamide-8, and polyamide-3.

As the fatty acid, one that is solid at ordinary temperature can be used, and examples thereof may include myristic acid, palmitic acid, stearic acid, behenic acid, and 12-hydroxystearic acid. As the salt of a fatty acid, a calcium salt, a magnesium salt, an aluminum salt, or the like, of such a fatty acid can be used.

Representative specific examples of the organic modified clay mineral may include dimethyl distearyl ammonium hectorite, dimethyl alkyl ammonium hectorite, benzyl dimethyl stearyl ammonium hectorite, and distearyl dimethyl ammonium chloride-treated magnesium aluminum silicate. Preferred examples of commercially available product of the organic modified clay mineral may include BENTONE 27 (benzyl dimethyl stearyl ammonium chloride-treated hectorite, available from Elementis Japan), and BENTONE 38 (distearyl dimethyl ammonium chloride-treated hectorite, available from Elementis Japan).

The oil component thickener is contained in an amount in the range from 0.1 to 40 mass %, more preferably in the range from 0.2 to 30 mass %, and even more preferably in the range from 0.4 to 15 mass % relative to the total amount of the composition. If the content of the (e) oil component thickener is less than 0.1 mass %, it is difficult to provide sufficient stability. On the other hand, if the content of the (e) oil component thickener exceeds 40 mass %, the composition becomes highly sticky and heavy when it is spread over the skin, and this is not preferable in view of usability.

It should be noted that the refractive indices in the disclosure are values measured at 25° C. using AUTOMATIC REFRACTOMETER, available from Rudolph Research Analytical, except that literature values are given with respect to the powders.

It is preferred that the transparent composition of the disclosure be solid. The term "solid" as used herein means that the composition has no fluidity at ordinary temperature (15° C. to 25° C.) and ordinary pressure. The composition may be provided in the form of a stick, a dish, an ointment, or the like. In particular, the composition in the form of a stick is easy to use since it is not necessary to use fingers or a tool and the composition can directly be applied to the skin. Further, the appearance of a transparent stick is preferred since it is appealing and one can tell that transparent finish is provided just by looking at the product.

The term "transparent" as used herein refers to that, when transmittance of a measurement sample prepared by melt filling a base that contains no powder other than the component (d) of the transparent composition of the disclosure in a plastic cell with an optical path length of 10 mm×an optical path width of 10 mm is measured with a spectrophotometer (U-4100, available from HITACHI), the transmittance is 70% or more in a wavelength region of light of 700 nm, and encompasses a colored composition as long as it has a transmittance within this range.

Besides the essential components described above, the transparent composition of the disclosure can contain optional components as long as the effects of the disclosure are not impaired. Any types of transparent cosmetics can be produced by adding optional components that are commonly contained in cosmetics according to conventional methods.

The optional component may include an oil component, a higher alcohol, a POE (polyoxyethylene)/POP (polyoxypropylene) dimethyl ether, a surfactant, a moisturizing agent, a chelating agent, an anti-oxidant, and an oil-soluble chemical, other than the components (a) to (e) described above, and may be contained in an amount within a range where transparency of the composition is not impaired.

Examples of animal and vegetable oils and fats include cocoa fat, coconut oil, hardened coconut oil, palm oil, palm kernel oil, japan wax kernel oil, hardened oil, japan wax, and hardened castor oil.

Examples of waxes include beeswax, candelilla wax, cotton wax, carnauba wax, bayberry wax, ibota wax, whale wax, montan wax, rice bran wax, lanolin, kapok wax, lanolin acetate, liquid lanolin, sugarcane wax, lanolin fatty acid isopropyl ester, hexyl laurate, reduced lanolin, hojova wax, hard lanolin, shellac wax, POE lanolin alcohol ether, POE lanolin alcohol acetate, POE cholesterol ether, lanolin fatty acid polyethylene glycol, POE hydrogenated lanolin alcohol ether, ceresin, and microcrystalline wax.

Examples of hydrocarbon oils include liquid paraffin, ozokerite, squalane, pristane, paraffin, squalene, and vaseline.

Examples of the higher alcohols include those having an alkyl group with a carbon number in the range from 6 to 20, and specifically include caproyl alcohol, capryl alcohol, lauryl alcohol, myristyl alcohol, cetyl alcohol, stearyl alcohol, and arachidyl alcohol. The alkyl group may be branched, and may have an unsaturated bond, hydroxyl group, carboxyl group, or a substituent group, such as phenyl group.

Examples of the POE/POP dimethyl ether include alkylene oxide derivatives, etc., taught in Japanese Unexamined Patent Publication No. 2003-113023.

Examples of lipophilic nonionic surfactant include a sorbitan fatty acid ester (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, or diglycerol sorbitan tetra-2-ethylhexylate); a glycerol polyglycerol fatty acid (such as glycerol monocottonseed fatty acid, glycerol monoerucate, glycerol sesquioleate, glycerol monostearate, α,α'-glycerol oleate pyroglutamate, or glycerol monostearate malate); a propylene glycol fatty acid ester (such as propylene glycol monostearate); a hardened castor oil derivative; and a glycerol alkyl ether.

Examples of hydrophilic nonionic surfactant include a POE-sorbitan fatty acid ester (such as POE-sorbitan monooleate, POE-sorbitan monostearate, POE-sorbitan monooleate, or POE-sorbitan tetraoleate); a POE sorbitol fatty acid ester (such as POE-sorbitol monolaurate, POE sorbitol monooleate, POE-sorbitol pentaoleate, or POE-sorbitol monostearate); a POE-glycerin fatty acid ester (such as POE-glycerin monostearate, POE-glycerin monoisostearate, or POE-glycerin triisostearate); a POE-fatty acid ester (such as POE-distearate, POE-monodioleate, or ethylene glycol distearate); a POE-alkyl ether (such as POE-lauryl ether, POE-oleyl ether, POE-stearyl ether, POE-behenyl ether, POE-2-octyldodecyl ether, or POE-cholestanol ether); a POE/POP-alkyl ether (such as POE/POP-cetyl ether, POE/POP-2-decyltetradecyl ether, POE/POP-monobutyl ether, POE/POP-hydrogenated lanolin, or POE/POP-glycerin ether); a POE-castor oil hardened castor oil derivative (such as POE-castor oil, POE-hardened castor oil, POP-hardened castor oil monoisostearate, POP-hardened castor oil triisostearate, POE-hardened castor oil monopyroglutamate monoisostearate diester, or POE-hardened castor oil maleate); a POE-beeswax/lanolin derivative (such as POP-sorbitol beeswax); an alkanolamide (such as coconut oil fatty acid diethanolamide, lauric acid monoethanolamide, or fatty acid isopropanolamide); a POE-propylene glycol fatty acid ester; a POE-alkylamine; a POE-fatty acid amide; a sucrose fatty acid ester; and a trioleyl phosphate.

Examples of the moisturizing agent include polyethylene glycol, propylene glycol, glycerin, 1,3-butylene glycol, xylitol, sorbitol, maltitol, chondroitin sulfate, hyaluronic acid, mucoitin sulfate, colanic acid, atelocollagen, cholesteryl-12-hydroxystearate, sodium lactate, bile salt, d,1-pyrrolidone carboxyliate, short chain soluble collagen, diglycerin (EO) PO((ethylene oxide)propyleneoxide) adduct, Rosa roxburghii extract, yarrow extract, melilot extract, trehalose, erythritol, and POE/POP random copolymer metylether.

Examples of the chelating agent include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of vitamin include vitamins A, B1, B2, B6, C, and E and derivatives thereof, pantothenic acid and derivatives thereof, and biotin.

Examples of antioxidant include a tocopherol, dibutylhydroxytoluene, butylhydroxyanisole, and a gallic acid ester.

Examples of antioxidation aid include phosphoric acid, citric acid, ascorbic acid, maleic acid, malonic acid, succinic acid, fumaric acid, cephalin, hexametaphosphite, phytic acid, and ethylenediaminetetraacetic acid.

Examples of other components that can be added include an antiseptic (such as methyl paraben, ethyl paraben, butyl paraben, and phenoxyethanol); an anti-inflammatory agent (such as a glycyrrhizic acid derivative, a glycyrrhetinic acid derivative, thiotaurine, hypotaurine, hinokitiol, zinc oxide, or alantoin); a whitening agent (such as Saxifraga stolonifera extract, albutin, tranexamic acid, L-ascorbic acid, L-ascorbic acid phosphate magnesium salt, L-ascorbic acid glucoside, and potassium 4-methoxysalicylate); and various extracts (such as phellodendron bark, coptis japonica, lithospermi radix, paeonia lactiflora, swertia herb, birch, sage, eriobotrya japonica, carrot, aroe, mallow, iris, grape, coix seed, loofa, lily, saffron, enidium rhizome, ginger, hypericum erectum, ononis, garlic, capsicum annum, citrus reticulata peel, japanese angelica root, and seaweed); an activator agent (such as royal jelly, a photosensitizer, and a cholesterol derivative); and a blood circulation promoter.

The transparent cosmetic according to the disclosure can also contain, as a solidification aid, an oil-based gelling agent component, such as dextrin palmitate, glyceryl behenate/eicosadioate, polyamide-3, polyamide-8, 2-ethylhexanoyl glutamic acid butylamide, or N-2-ethylhexanoyl-L-glutamic acid dibutylamide, in an amount within a rage were transparency of the cosmetic is maintained.

The form in which the transparent cosmetic of the disclosure is provided is not particularly limited; however, the transparent cosmetic of the disclosure is preferably provided in the form of gel or solid. The product containing the transparent cosmetic of the disclosure is not particularly limited, and examples thereof may include makeup cosmetics, such as foundations, lip stick, lip gloss, lip cream, and eye shadow, makeup base, sunscreen, skincare cosmetics, hair stick, body cosmetics, antiperspirant cosmetics, and hair cosmetics, such as pomade. The transparent cosmetic of the disclosure is preferably used as a transparent solid cosmetic filled in a container or in the form of a stick.

The transparent composition of the disclosure and a cosmetic using the transparent composition can be prepared according to a conventional method. For example, the above-described components may be melted and dispersed at temperatures in the range from 70 to 100° C., poured into a desired mold or container, and then cooled to solidify.

EXAMPLES

Next, the present disclosure is described in further detail with reference to examples. The examples given below are not intended to limit the present disclosure. Amounts of the individual components are given in mass % unless otherwise noted.

It should be noted that the examples and comparative examples were produced according to formulations shown in Tables 1 to 3 using a conventional method. Specifically, samples of the examples and comparative examples were obtained by adding the oil component thickener(s) (if present) to the oil components, heating and melting them at temperatures in the range from 80 to 130° C., adding the remaining components (such as the UV absorbent, the powder, etc.) and uniformly dispersing the components using a homomixer, degassing the resulting mixture, and then solidifying the mixture at room temperature.

Refractive Index

Refractive indices were measured at 25° C. using AUTOMATIC REFRACTOMETER available from Rudolph Research Analytical.

Transparency

Transmittance of a measurement sample prepared by melt filling a base, which contained no powder, of each of examples and comparative examples in a plastic cell with an optical path length of 10 mm×an optical path width of 10 mm was measured with a spectrophotometer (U-4100, available from HITACHI) in a wavelength region of light of 700 nm.

UV Protection Effect After Bathing in Water

A drop of each sample in an amount of 2 mg/cm$^2$ was put on a measurement plate (S plate) (a 5×5-cm V-groove PMMA plate, SPFMASTER-PA01), spread using a finger for 60 seconds, and dried for 15 minutes. Then, absorbance of the thus formed layer of the sample was measured using a self-recording spectrophotometer, U-4100, available from HITACHI. Using a measurement plate with nothing applied thereto as a control, absorbance (Abs) was calculated according to the equation shown below:

$$Abs=-\log(T/To),$$

where T is a transmittance of the sample and To is a transmittance of the measurement plate with nothing applied thereto.

The plate having been subjected to the measurement was sufficiently immersed in water having a hardness in the range from 50 to 500 and left still in the water for 30 minutes. Thereafter, the plate was dried for about 15 to 30 minutes until water droplets on the surface of the plate disappeared, and then absorbance was measured again. Then, an Abs change rate was calculated (according to the equation shown below) from integrated Abs values (within a wavelength range from 280 to 400 nm) before and after the bathing in water as a UV protection capability improving effect.

UV protection capability improving effect:

Abs change rate (%)=(integrated Abs value after bathing in water)/(integrated Abs value before bathing in water)× 100

TABLE 1

| Classification | Names of all components | Refractive index | Ex. 1 | Ex. 2 | Ex. 3 | Ex. 4 | Ex. 5 |
|---|---|---|---|---|---|---|---|
| (a) UV absorbent | t-Butyl methoxydibenzoylmethane | | | 2 | 3 | 3 | 3 |
| | Ethylhexyl methoxycinnamate | | 3 | 3 | 5 | 5 | 5 |
| | Octocrylene | | 2 | 5 | 5 | 5 | 5 |
| | Diethylamino hydroxybenzoyl hexyl benzoate | | 1 | 1 | 2 | 2 | 2 |
| | Bis-ethylhexyloxyphenol methoxyphenyl triazine | | 1 | 1 | 2 | 2 | 2 |
| | Homosalate | | | | | 10 | 10 | 10 |
| | Polysilicone-15 | | | | | | |
| (b) High refractive index oil component | Diphenylsiloxy phenyl trimethicone | 1.5 | 15 | 25 | 50 | 50 | 50 |
| | Trimethyl pentaphenyl polysiloxane | 1.58 | | | | | |
| (c) Low refractive index oil component | Diisopropyl sebacate | 1.431 | 50 | 40 | 15 | 15 | 15 |
| | Isopropyl myristate | 1.435 | 26 | 21 | 6 | 6 | 6 |
| | Macadamia nut oil | 1.466 | | | | | |
| (d) Powder | Silica | 1.45 | 2 | | | | |
| | Silica dimethyl silylate | 1.46 | | 2 | | | |
| | Methyl methacrylate cross polymer | 1.49 | | | 2 | | |
| | Silica-coated IPDI/poly(1,4-butanediol)-14 cross polymer | 1.49 | | | | 2 | |
| | Cellulose | 1.49 | | | | | 2 |
| | Silica-coated HDI/trimethylol hexyl lactone cross polymer | 1.5 | | | | | |
| | Nylon-12 | 1.53 | | | | | |
| | Silica dimethyl silylate-coated polyethylene | 1.53 | | | | | |
| Physical property Evaluation | Refractive index of (b) + (c) | | 1.444 | 1.452 | 1.480 | 1.480 | 1.480 |
| | Transmittance (700 nm) | | 95% | 99% | 99% | 98% | 93% |
| | UV protection effect after bathing in water | | 105% | 104% | 107% | 104% | 105% |

| Classification | Names of all components | Ex. 6 | Ex. 7 | Ex. 8 | Ex. 9 | Comp. Ex. 1 |
|---|---|---|---|---|---|---|
| (a) UV absorbent | t-Butyl methoxydibenzoylmethane | 3 | 3 | 3 | 3 | 3 |
| | Ethylhexyl methoxycinnamate | 5 | 10 | 10 | 3 | 3 |
| | Octocrylene | 5 | 5 | 5 | 5 | 5 |
| | Diethylamino hydroxybenzoyl hexyl benzoate | 2 | 2 | 2 | 2 | 2 |
| | Bis-ethylhexyloxyphenol methoxyphenyl triazine | 2 | 2 | 2 | 2 | 2 |
| | Homosalate | 10 | 10 | 10 | 10 | 10 |
| | Polysilicone-15 | | 5 | 5 | | |
| (b) High refractive index oil component | Diphenylsiloxy phenyl trimethicone | 35 | 16 | 16 | 16 | 12 |
| | Trimethyl pentaphenyl polysiloxane | 6 | 20 | 20 | | |
| (c) Low refractive index oil component | Diisopropyl sebacate | | | | | 30 |
| | Isopropyl myristate | 10 | 5 | 5 | | 33 |
| | Macadamia nut oil | | | | 57 | |

TABLE 1-continued

|  |  |  |  |  |  |  |  |
|---|---|---|---|---|---|---|---|
| (d) Powder | Silica |  |  |  |  |  |  |
|  | Silica dimethyl silylate |  |  |  |  |  |  |
|  | Methyl methacrylate cross polymer |  |  |  |  | 2 |  |
|  | Silica-coated IPDI/poly(1,4-butanediol)-14 cross polymer |  |  |  |  |  |  |
|  | Cellulose |  |  |  |  |  |  |
|  | Silica-coated HDI/trimethylol hexyl lactone cross polymer | 2 |  |  |  |  |  |
|  | Nylon-12 |  | 2 |  |  |  |  |
|  | Silica dimethyl silylate-coated polyethylene |  |  | 2 |  |  |  |
| Physical property | Refractive index of (b) + (c) | 1.496 | 1.531 | 1.531 | 1.473 | 1.444 |  |
| Evaluation | Transmittance (700 nm) | 96% | 96% | 97% | 99% | 99% |  |
|  | UV protection effect after bathing in water | 104% | 107% | 104% | 106% | 94% |  |

TABLE 2

|  |  | Refractive index | Ex. 10 | Ex. 11 | Ex. 12 | Ex. 13 | Ex. 14 | Ex. 15 | Comp. Ex. 2 |
|---|---|---|---|---|---|---|---|---|---|
| (a) UV absorbent | t-Butyl methoxydibenzoylmethane |  | 3 | 3 | 3 | 3 | 3 | 3 | 3 |
|  | Ethylhexyl methoxycinnamate |  | 3 | 3 | 3 | 3 | 3 | 3 | 3 |
|  | Octocrylene |  | 5 | 5 | 5 | 5 | 5 | 5 | 5 |
|  | Diethylamino hydroxybenzoyl hexyl benzoate |  | 2 | 2 | 2 | 2 | 2 | 2 | 2 |
|  | Bis-ethylhexyloxyphenol methoxyphenyl triazine |  | 2 | 2 | 2 | 2 | 2 | 2 | 2 |
|  | Homosalate |  | 10 | 10 | 10 | 10 | 10 | 10 | 10 |
|  | Ethylhexyl salicylate |  | 5 | 5 | 5 | 5 | 5 | 5 | 5 |
| (b) High refractive index oil component | Diphenylsiloxy phenyl trimethicone | 1.5 | 40 | 35 | 35 | 35 | 35 | 35 | 40 |
| (c) Low refractive index oil component | Diisopropyl sebacate | 1.431 | 15 | 15 | 15 | 15 | 15 | 15 | 15 |
|  | Hydrogenated polydecene | 1.46 | 14 | 10 | 10 | 9 | 7 | 17 | 15 |
| (e) Oil component thickener | 12-hydroxystearic acid |  |  | 7 | 7 |  | 7 |  |  |
|  | Dibutyl lauroyl glutamide |  |  | 2 |  |  |  |  |  |
|  | Dibutyl ethylhexanoyl glutamide |  |  |  | 2 |  |  |  |  |
|  | Polyamide-8 |  |  |  |  | 10 |  |  |  |
|  | Glyceryl behenate/eicosadioate |  |  |  |  |  | 5 |  |  |
|  | Dextrin palmitate |  |  |  |  |  |  | 2 |  |
| (d) Powder | Methyl methacrylate cross polymer | 1.49 | 1 | 1 | 1 | 1 | 1 | 1 |  |
| Physical property | Refractive index of (b) + (c) |  | 1.477 | 1.476 | 1.476 | 1.476 | 1.477 | 1.475 | 1.477 |
| Evaluation | Transmittance (700 nm) |  | 99% | 98% | 97% | 99% | 91% | 96% | 99% |
|  | UV protection effect after bathing in water |  | 106% | 108% | 109% | 107% | 111% | 106% | 95% |

TABLE 3

|  |  | Refractive index | Ex. 13 | Comp. Ex. 3 | Comp. Ex. 4 |
|---|---|---|---|---|---|
| (a) UV absorbent | t-Butyl methoxydibenzoylmethane |  | 3 | 3 | 3 |
|  | Ethylhexyl methoxycinnamate |  | 3 | 3 | 3 |
|  | Octocrylene |  | 5 | 5 | 5 |
|  | Diethylamino hydroxybenzoyl hexyl benzoate |  | 2 | 2 | 2 |
|  | Bis-ethylhexyloxyphenol methoxyphenyl triazine |  | 2 | 2 | 2 |
|  | Homosalate |  | 10 | 10 | 10 |
|  | Ethylhexyl salicylate |  | 5 | 5 | 5 |
| (b) High refractive index oil component | Diphenylsiloxy phenyl trimethicone | 1.5 | 35 |  | 59 |
| (c) Low refractive index oil component | Diisopropyl sebacate | 1.431 | 15 | 50 |  |
|  | Hydrogenated polydecene | 1.46 | 9 | 19 |  |
| (e) Oil component thickener | 12-hydroxystearic acid |  |  |  |  |
|  | Dibutyl lauroyl glutamide |  |  |  |  |
|  | Dibutyl ethylhexanoyl glutamide |  |  |  |  |
|  | Polyamide-8 |  | 10 | 10 | 10 |
|  | Glyceryl behenate/eicosadioate |  |  |  |  |
|  | Dextrin palmitate |  |  |  |  |

TABLE 3-continued

|  | Names of all components | Refractive index | Ex. 13 | Comp. Ex. 3 | Comp. Ex. 4 |
|---|---|---|---|---|---|
| (d) Powder | Methyl methacrylate cross polymer | 1.49 | 1 | 1 | 1 |
| Physical property | Refractive index of (b) + (c) |  | 1.476 | 1.439 | 1.500 |
| Evaluation | Transmittance (700 nm) |  | 99% | 12% | 56% |

As shown in Table 1, the transparent compositions of the disclosure exhibited a characteristic that the UV protection effect was improved after bathing in water while maintaining high transparency. In contrast, with respect to Comparative Example 1, which did not contain the (d) powder, transparency was maintained, but the UV protection effect was degraded after bathing in water.

Further, as shown in Table 2, the transparent compositions of the disclosure which contained the oil component thickener (Examples 11 to 15) also exhibited high transparency and a characteristic that the UV protection effect was improved after bathing in water, similarly to Example 10 which did not contain the oil component thickener. In contrast, with respect to Comparative Example 2, which contained the oil component thickener but did not contain the (d) powder, the UV protection effect was degraded. Further, as shown in Table 3, Comparative Example 3, which did not contain the (b) high refractive index oil component, and Comparative Example 4, which did not contain the (c) low refractive index oil component, were not transparent.

The following transparent cosmetics were produced according to conventional methods.

Formulation Example 1: Makeup Base

| Ethylhexyl methoxycinnamate | 5% |
|---|---|
| Homosalate | 5% |
| t-Butyl methoxydibenzoylmethane | 2% |
| Bis-ethylhexyloxyphenol methoxyphenyl triazine | 1% |
| Polyamide-8 | 20% |
| Cetyl ethylhexanoate | 40% |
| Diphenylsiloxy phenyl trimethicone | 15% |
| Stearyl glycyrrhetinate | 0.1% |
| Tocopherol | 0.5% |
| Silica | 5% |
| Dipropylene glycol | 1% |
| Triethylhexanoin | balance |

Formulation Example 2: Partial Foundation

| Hydroxystearic acid | 7% |
|---|---|
| Ethylhexyl methoxycinnamate | 10% |
| Ethylhexyl salicylate | 5% |
| Diethylamino hydroxybenzoyl hexyl benzoate | 2% |
| Bis-ethylhexyloxyphenol methoxyphenyl triazine | 1% |
| Dibutyl lauroyl glutamide | 2% |
| Polyamide-8 | 3% |
| Methyl methacrylate cross polymer | 10% |
| Trimethyl pentaphenyl polysiloxane | 3% |
| Hydrogenated polydecene | 20% |
| Cellulose | 0.5% |
| Diphenylsiloxy phenyl trimethicone | balance |

Formulation Example 3: Lip Gloss

| Diethylamino hydroxybenzoyl hexyl benzoate | 2% |
|---|---|
| Ethylhexyl methoxycinnamate | 10% |
| Bis-ethylhexyloxyphenol methoxyphenyl triazine | 1% |
| Trimethyl pentaphenyl polysiloxane | 6% |
| Caprylyl methicone | 20% |
| Isopropyl myristate | 5% |
| Isostearic acid | 0.01% |
| Silica dimethyl silylate | 0.5% |
| Polyamide-8 | 10% |
| Diphenylsiloxy phenyl trimethicone | balance |

Formulation Example 4: Sunscreen

| Ethylhexyl salicylate | 5% |
|---|---|
| t-Butyl methoxydibenzoylmethane | 2% |
| Bis-ethylhexyloxyphenol methoxyphenyl triazine | 1% |
| Octocrylene | 5% |
| Ethylhexyl triazone | 1.5% |
| Homosalate | 10% |
| Diisopropyl sebacate | 15% |
| PPG-3 dipivalate | 15% |
| Sorbitan sesquiisostearate | 0.01% |
| Dextrin palmitate | 2% |
| IPDI/poly(1,4-butanediol)-14 cross polymer | 1% |
| Dibutyl lauroyl glutamide | 2% |
| Dibutyl ethylhexanoyl glutamide | 2% |
| PEG/PPG-14/7 dimethyl ether | 0.5% |
| Diphenylsiloxy phenyl trimethicone | balance |

Formulation Example 5: Makeup Veil

| Homosalate | 5% |
|---|---|
| Ethylhexyl salicylate | 5% |
| Diethylamino hydroxybenzoyl hexyl benzoate | 2% |
| Bis-ethylhexyloxyphenol methoxyphenyl triazine | 1% |
| Isododecane | 20% |
| Silica dimethyl silylate | 1% |
| Trimethylsiloxysilicate | 0.1% |
| Diphenylsiloxy phenyl trimethicone | 20% |
| Isopropyl myristate | 15% |
| Alcohol | 10% |
| Ethylhexyl palmitate | balance |

The transparent cosmetics of the above-described formulation examples have excellent transparency of the appearance of the base, provide good feel during use, and have a characteristic that the UV protection effect is improved after bathing in water.

The invention claimed is:

1. A transparent composition comprising:
   (a) a UV absorbent;
   (b) an oil component having a refractive index in the range from 1.5 to 1.7;
   (c) an oil component having a refractive index of not less than 1.3 and less than 1.5;
   (d) a powder having a refractive index in the range from 1.45 to 1.55; and
   (e) an oil component thickener,
   wherein a mixed oil component obtained by mixing the (b) oil component having a refractive index in the range from 1.5 to 1.7 and the (c) oil component having a refractive index of not less than 1.3 and less than 1.5 has a refractive index in the range from 1.44 to 1.56,
   wherein the (b) oil component having a refractive index in the range from 1.5 to 1.7 comprises at least one selected from a group consisting of hydrogenated polyisobutene, trimethylpentaphenyl polysiloxane, diphenylsiloxy phenyl trimethicone, diphenyl dimethicone, phytosteryl macadamia nut fatty acid and phytosteryl isostearate,
   wherein the (c) oil component having a refractive index of not less than 1.3 and less than 1.5 comprises at least one selected from a group consisting of diisopropyl sebacate, triethylhexanoine, hydrogenated polydecene, glyceryl tricaprylate-caprate, cetyl 2-ethylhexanoate, trimethylolpropane trioctanoate, α-olefin oligomer, glyceryl diisostearate, polyglyceryl triisostearate, isododecane, isohexadecane, light isoparaffin and polyoxyethylene-polyalkylsiloxane,
   wherein the (d) powder having a refractive index in the range from 1.45 to 1.55 comprises at least one selected from a group consisting of dimethyl silylated silica, polymethyl methacrylate, HDI/trimethylol hexyl lactone cross polymer, IPDI/poly (1,4-butane diol)-14 cross polymer and cellulose, and
   wherein the (e) oil component thickener comprises at least one selected from a first group consisting of dibutyl lauroyl glutamide, dibutyl ethyl hexanoyl glutamide, polyamide-8, and (behenic acid/eicosane diacid) glyceryl, and optionally further comprises at least one selected from a second group consisting of 12-hydroxy stearic acid and palmitate dextrin.

2. The transparent composition as claimed in claim 1, wherein a mass ratio of the (d) powder having a refractive index in the range from 1.45 to 1.55 relative to the (a) UV absorbent is not less than 0.01 and not more than 1.

3. The transparent composition as claimed in claim 1 provided in a solid form.

4. The transparent composition as claimed in claim 3 provided in a stick form.

5. A transparent cosmetic comprising the transparent composition as claimed in claim 1 as a base.

6. The transparent composition as claimed in claim 2 provided in a solid form.

7. The transparent composition as claimed in claim 6 provided in a stick form.

8. A transparent cosmetic comprising the transparent composition as claimed in claim 2 as a base.

* * * * *